United States Patent [19]

Pauls et al.

[11] Patent Number: 5,563,128
[45] Date of Patent: *Oct. 8, 1996

[54] PHOSPHONATE DERIVATIVES OF LIPOPHILIC AMINES

[75] Inventors: Henry W. Pauls, Collegeville; Yong-Mi Choi, Jeffersonville; Dilip V. Amin, Lansdale, all of Pa.

[73] Assignee: Rhone-Poulenc Rorer Pharmaceuticals Inc., Collegeville, Pa.

[*] Notice: The term of this patent shall not extend beyond the expiration date of Pat. No. 5,441,946.

[21] Appl. No.: 435,020

[22] Filed: May 4, 1995

Related U.S. Application Data

[62] Division of Ser. No. 227,803, Apr. 14, 1994, Pat. No. 5,441,946.

[51] Int. Cl.$^6$ .......... A61K 31/675; A61K 31/66
[52] U.S. Cl. .......... 514/80; 514/79; 514/82; 514/114; 546/22; 546/23; 548/113; 548/413
[58] Field of Search .......... 514/114, 82, 79, 514/80; 548/113, 413; 546/22, 23

[56] References Cited

U.S. PATENT DOCUMENTS 5,441,946  8/1995  Pauls et al. .......... 514/114

Primary Examiner—Amelia Owens
Attorney, Agent, or Firm—James A. Nicholson; Raymond S. Parker, III; Martin F. Savitzky

[57] ABSTRACT

This invention relates to a class of novel phosphonate derivatives of lipophilic amines which exhibit squalene synthase inhibition properties. More specifically the compounds are bis aryl cycloalkylamino and azacycloalkyl phosphonates. Compounds of this invention reduce levels of serum cholesterol in the body without significantly reducing mevalonic metabolite synthesis. This invention relates also to pharmacological compositions and method of treatment for lowering serum cholesterol levels using the compounds of this invention.

22 Claims, 1 Drawing Sheet

PHOSPHONATE DERIVATIVES OF LIPOPHILIC AMINES

This is a divisional of application Ser. No. 08/227,803 filed on Apr. 14, 1994 now U.S. Pat. No. 5,441,946.

FIELD OF THE INVENTION

The present invention relates to a class of novel compounds useful in the treatment of diseases associated with undesirable cholesterol levels in the body, and particularly diseases of the cardiovascular system, such as atherosclerosis. Compounds of the present invention may also be useful in treating fungal infections.

Only about 7% of the total body cholesterol circulates in the plasma, where it has been linked to atherosclerosis. The remaining 93% is located in cells, where it performs vital structural and metabolic functions. Excluding the diet, which accounts for approximately one-third of the total body cholesterol, the cells obtain the necessary cholesterol by endogenous biosynthesis (FIG. 1) or by removing low density lipoprotein (LDL) from the bloodstream. Approaches to the control of plasma cholesterol levels have been varied, however it has been shown that inhibiting endogenous cholesterol biosynthesis forces the cell to rely more on LDL uptake to satisfy their cholesterol requirements. Increased LDL uptake by cells, especially liver cells, has been shown to lower plasma cholesterol levels.

Squalene synthase is a microsomal enzyme that catalyzes the reductive dimerization of two molecules of farnesyl diphosphate to form squalene. While farnesyl diphosphate serves as the precursor to several other biologically important compounds, squalene is utilized only for cholesterol biosynthesis. Consequently, this is the first totally committed step in the biosynthesis of cholesterol (see FIG. 1). Inhibition at this step would stop only de novo cholesterol synthesis while allowing other essential pathways to isopentenyl tRNA, the prenylated proteins, ubiquinone, and dolichol to proceed unimpeded.

Inhibition of HMG-CoA reductase, an enzyme positioned early in the cholesterol biosynthetic pathway, results in a decrease of de novo cholesterol biosynthesis and an accompanying up-regulation of LDL receptors. However due to a large induction in the amount of the HMG-CoA reductase enzyme, the effect of this inhibition is blunted somewhat and the maximum LDL cholesterol reductions attainable are limited. Since inhibition of squalene synthase does not cause the same amount of enzyme induction (HMG-CoA reductase or squalene synthase), its inhibition results in a greater reduction of de novo cholesterol biosynthesis. This translates into more up-regulation of LDL receptors than is seen with an HMG-CoA reductase inhibitor and greater efficacy for lowering circulating LDL levels.

Reported Developments

The literature describes the cholesterol biosynthetic pathway and possible means for the inhibition of squalene synthase. In a series of papers including *J. Am. Chem. Soc.*, 1982, 104, 7376–7378 and *J. Am. Chem. Soc.*, 1989, 111, 3734–3739, C. Dale Poulter, et al disclose that ammonium substituted cyclopropyl polyene compounds mimic the topological and electrostatic properties of the primary cation and tertiary cation of presqualene diphosphate and in the presence of phosphate buffer, inhibit squalene synthase. Scott A. Biiler et al in *J. Med. Chem.*, 1988, 31, 1869–1871 disclose that a series of stable, non-ionizable analogues of farnesyl diphosphate, comprising phosphomethylene phosphate polyene compounds, inhibit squalene synthase.

Paul E. Schurr and Charles E. Day in in *Lipids*, Vol. 12, No. 1, 22–28 describe a compound known as U-41,792, 1-[p-(1-adamantyloxy)phenyl]piperidine, which is stated to cause a reduction in lower density lipoproteins, and is designated by the authors as having hypobetalipoproteinemia activity.

International Patent Application published under the Patent Cooperation Treaty having International Publication Number WO 92/15579 is directed to multicyclic tertiary amine polyaromatic squalene synthase inhibitors containing a multiazacyclic ring. U.S. Ser. No. 07/997,818, filed Dec. 29, 1992 is directed to cycloalkyl amine bis-aryl squalene synthase inhibitors. U.S. Ser. No. 08/65,966 is directed to aliphatic amino bis-aryl squalene synthase inhibitors. International Patent Application Number PCT/US93/12638, filed Dec. 29, 1993, is directed to cycloalkyl amine bis-aryl squalene synthase inhibitors. U.S. Ser. No. 08/083,117, filed Jun. 25, 1993, is directed to amino bi- and tri-carboxylic alkane bis-aryl squalene synthase inhibitors. Each of these applications is assigned to the same assignee as the present application.

U.S. Pat. No. 5, 135,935 assigned to Merck and Co., is directed to squalene synthase inhibitors which are aryl-oxadiazole-quinuclidines. International Patent Applications published under the Patent Cooperation Treaty having International Publication Numbers: WO 92/12159, 92/12158, 92/12157, 92/12156 92/12160 and 92/15579 and being assigned to Glaxo Group Ltd. are directed to bridged cyclic ketal derivatives for lowering the level of blood plasma cholesterol.

SUMMARY OF THE INVENTION

The present invention is directed to a class of novel phosphonate derivatives of lipophilic amines which exhibit squalene synthase inhibition properties.

More specifically, this invention comprises a class of chemical compounds described as bis-aryl and/or heteroaryl alkyl or cycloalkylamino phosphates. The compounds of this invention may be described by general formula I.

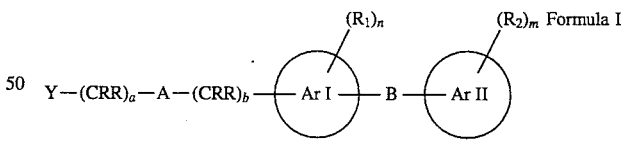

where:

A is O, S, NR, SO, $SO_2$ or a bond;

B is $(CRR)_{1-2}$, O, S, NR, SO, $SO_2$, RC=CR, C≡C, O=C or a bond;

Y is

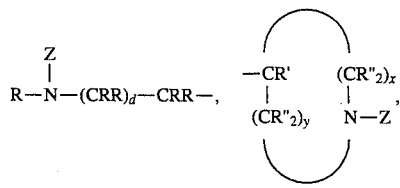

-continued

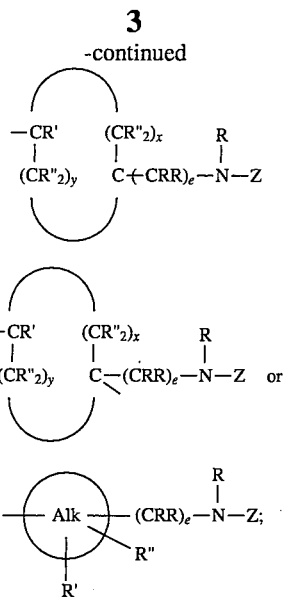

Z is

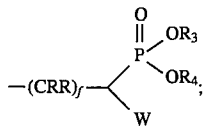

W is H,

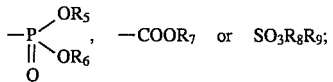

R is hydrogen or alkyl;

R' and R" are independently hydrogen, alkyl, alkoxy, hydroxy, halo, haloalkyl or phenyl;

R' and R" together may form a double bond;

$R_1$ and $R_2$ are independently hydrogen, alkyl, alkoxy, hydroxy, halo, haloalkyl or phenyl;

$R_3$, $R_4$, $R_5$, $R_6$, $R_7$, $R_8$ or $R_9$ are independently hydrogen, alkyl, aryl, aralkyl or —$CH_2OCOR$;

Alk is bi- or tri-carbocycloalkane;

Ar I and Ar II are independently a mono- or di-aryl or heteroaryl;

a and b are independently 0–3;

a+b is 0–4;

d is 0–3;

a+b+d is 1–3;

e is 0–3;

f is 1–6;

m and n are independently 0–2;

x is 1–6;

y is 0–2;

x+y is 3–6; and its stereoisomers, enantiomers, diastereoisomer and racemic mixtures; or a pharmaceutically acceptable salt thereof.

DETAILED DESCRIPTION AND PREFERRED EMBODIMENTS

Figure 1:
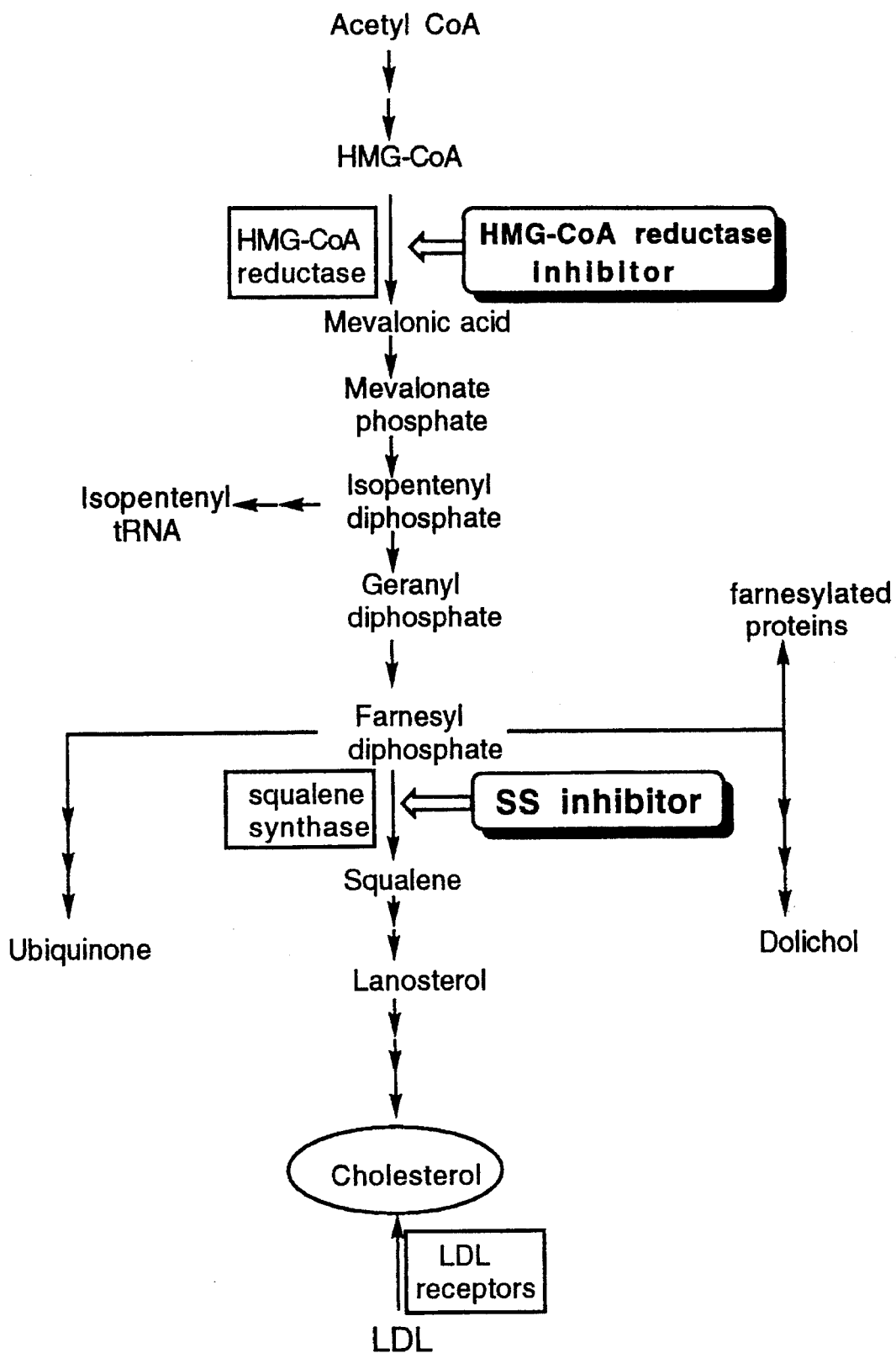
FIG. 1 is a schematic diagram of the biosynthetic pathway of cholesterol.

As employed above and throughout this disclosure, the following terms, unless otherwise indicated, shall be understood to have the following meanings:

"Aryl" means a monocylic or bicyclic carbocyclic or heterocyclic aromatic ring.

"Mono-aryl or heteroaryl" means a monocylic carbocyclic or heterocyclic aromatic ring. Preferred rings are substituted or unsubstituted pyrrole, thiophene, furan, imidazole, pyrazole, 1,2,4-triazole, pyridine, pyrazine, pyrimidine, pyridazine, thiazole, isothiazole, oxazole, isoxazole, s-triazine and benzene. Most preferred groups include phenyl, thienyl, pyridinyl, furyl and pyrimidinyl.

"Di-aryl or heteroaryl" means a bicyclic ring system composed of two fused carbocyclic and/or heterocyclic aromatic rings. Preferred bicyclic rings include substituted and unsubstituted indene, isoindene, benzofuran, dihydrobenzofuran, benzothiophene, indole, 1H-indazole, indoline, azulene, tetrahydroazulene, benzofuran, benzothiaphene, benzopyrazole, benzoimidazole, benzoxazole, benzothiazole, 1,3-benzodioxole, 1,4-benzodioxan, purine, naphthalene, tetralin, coumarin, chromone, chromene, 1,2-dihydrobenzothiopyran, tetrahydrobenzothiopyran, quinoline, isoquinoline, quinazoline, pyrido[3,4-b]-pyridine, and 1,4-benzisoxazine. Most preferred groups include naphthyl, benzoxazolyl, indolyl, benzothienyl, benzofuranyl, quinolinyl and benzothiazole.

"Alkyl" means a saturated aliphatic hydrocarbon, either branched- or straight-chained. Preferred alkyl is "lower alkyl" having about 1 to about 6 carbon atoms. Examples of alkyl include methyl, ethyl, n-propyl, isopropyl, butyl, sec-butyl, t-butyl, amyl and hexyl.

The preferred "aralkyl" groups are benzyl and phenethyl.

"Alkoxy" means an alkyl-O-group.

"Halo" means a halogen. Preferred halogens include chloride, bromide and fluoride.

The preferred haloalkyl group is trifluoromethyl.

"Bi-carbocycloalkane" refers to a ring system composed of two fused carbocyclic rings. Preferred bi-carbocyclic alkane rings include bicycio[2.2.1]heptane, bicyclo[2.2.2]octane, bicyclo[3.2.1]octane, bicyclo[3.2.2]nonane, bicyclo[3.3.1]nonane, bicyclo[4.2.1]nonane and bicyclo[2.2.2]octene.

"Tri-carbocycloalkane" refers to a ring system composed of three fused carbocyclic rings. Preferred tricarbocyclic alkane rings include tricyclo[3.3.1.1$^{3,7}$]decane, tricyclo[2.2.2.2$^{1,4}$]decane, tricyclo[3.2.2.1$^{1,4}$]decane and tricyclo[4.3.1.1$^{3,8}$]undecane.

The preferred compounds of this invention are described by the compounds of formula I where Ar I is phenyl and Ar II is phenyl, naphthyl, pyridyl, quinolinyl or benzoxazoyl.

The more preferred compounds of this invention are described by formulae II–VI.

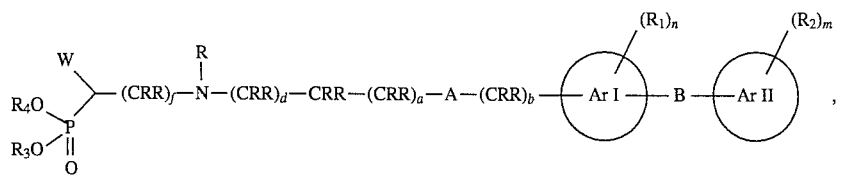
Formula II
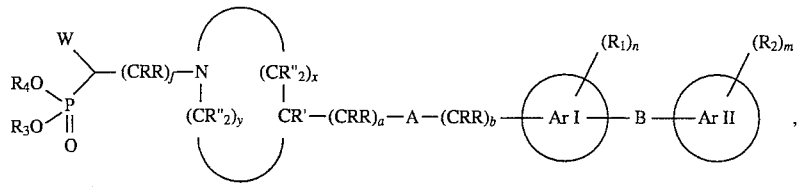
Formula III
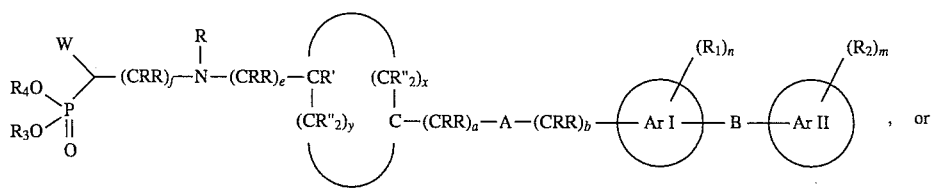
Formula IV , or
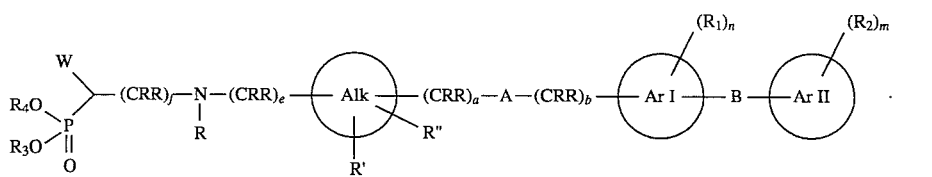
Formula V
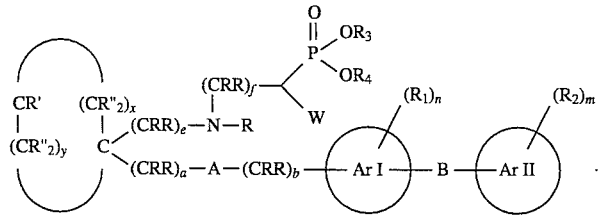
Formula VI
The most preferred compounds of this invention are described by Formulae VII–XIV.
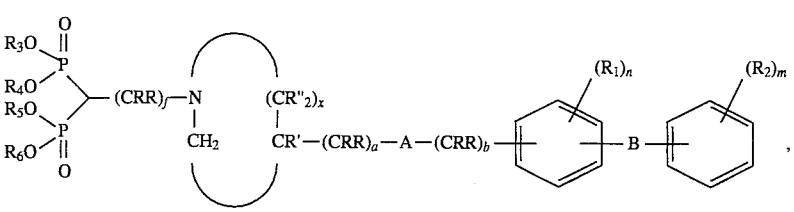
Formula VII
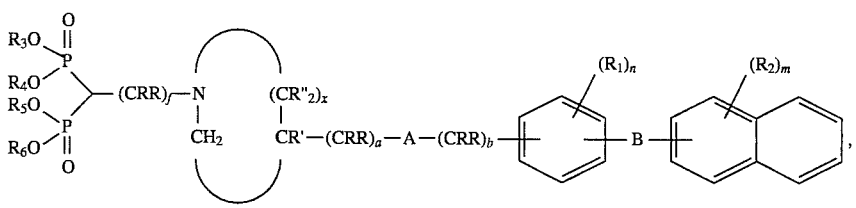
Formula VIII

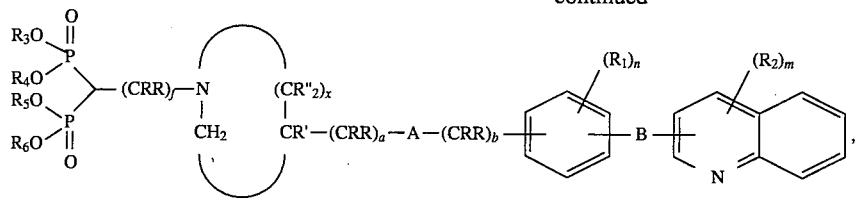
Formula IX
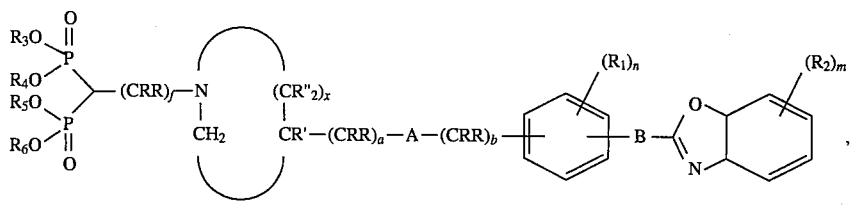
Formula X
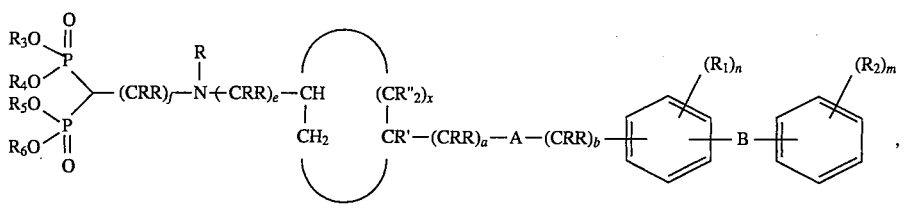
Formula XI
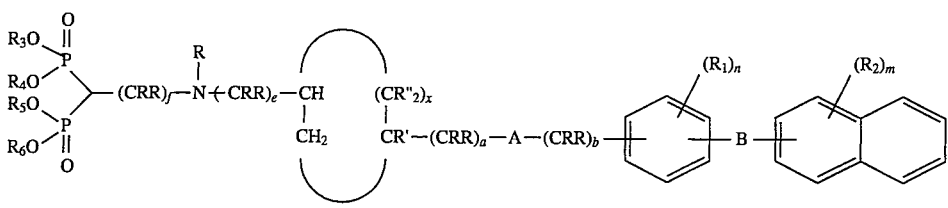
Formula XII
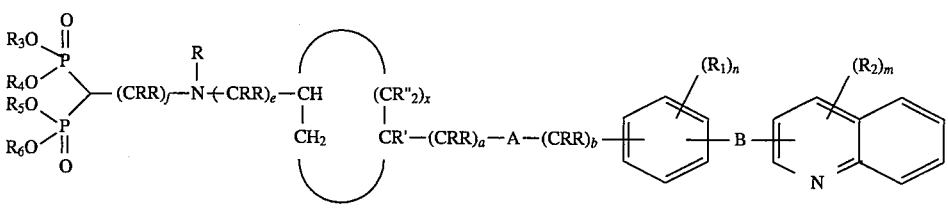
Formula XIII
or
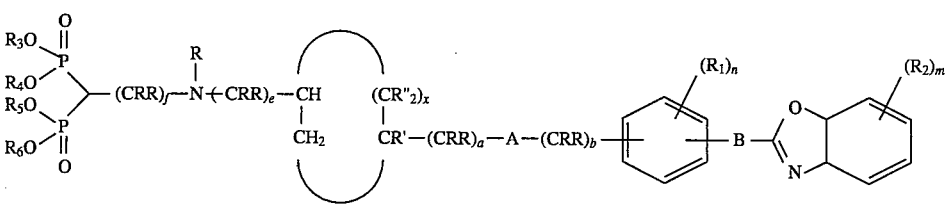
Formula XIV
The compounds of the present invention may be prpared by the following general methods.
STEP A1
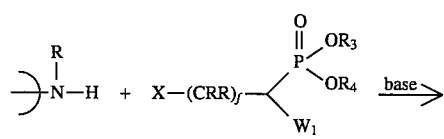
STEP A2
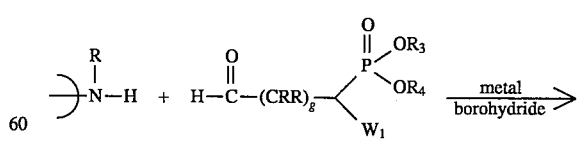
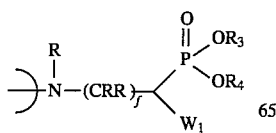

STEP B

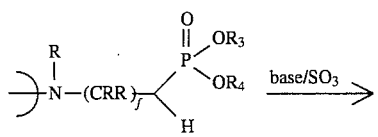

STEP C1

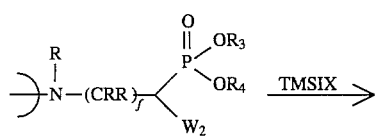

STEP C2

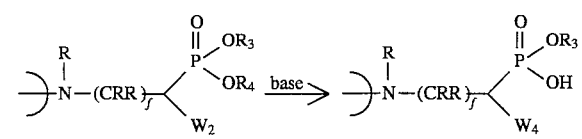

where:

X is tosyl, nosyl, bromide, chloride, iodide or mesyl;

f is as described above;

g is 2–5;

R is as described above;

$R_3$, $R_4$, $R_5$, $R_6$, $R_7$, $R_8$, and $R_9$ are independently alkyl, aryl, aralkyl or —$CH_2OCOR$;

$W_1$ is H, $PO_3R_5R_6$ or —$COOR_7$;

$W_2$ is H, —$COOR_7$, $SO_3H$ or $PO_3R_5R_6$;

$W_3$ is H, —COOH, $PO_3H_2$ or $SO_3H$; and $W_4$ is H, —COOH, $PO_3HR_5$ or $SO_3H$.

In general, the first step involves the preparation of lipophilic aminoalkyl phosphonate esters as shown in Step A1. The secondary or primary amine starting materials are in some cases commercially available but more often are prepared by methods described in copending application Ser. Nos. 08/065,966, 08/083,117, and PCT/US93/12638, which are all assigned to the same assignee as the present invention, and which are all incorporated herein by reference. The starting amines, preferably secondary amines, are treated with about 1 to about 1.5 molar equivalents, preferably about 1.2 equivalents, of a base such as sodium hydride, potassium hydride, lithium diisopropylamine (LDA) or potassium hexamethyldisilazide, preferably NaH, at about 0° C. to about room temperature for 20 to 40 minutes in a polar aprotic solvent then adding DMPU (dimethyltetrahydropyrimidinone) or HMPA (hexamethylphosphoramide) and stirring for about 30 minutes to one hour, most preferably one hour. Typical polar aprotic solvents include tetrahydrofuran (THF), dimethoxyethane (DME), acetonitrile, ether or dioxane. Preferred solvents are THF or DME. The alkylating agent, tosyl alkylphosphonate or bisphosphonate, or some other readily available halo alkylphosphonate or bisphosphonate, and tetrabutyl ammonium iodide in the chosen solvent is then introduced via cannula to the reaction flask and generally stirred overnight with heating. Suitable temperature ranges are room temperature to about 100° C., but preferably the temperature is in the range of about 40° C. to about 80° C. Typical reaction time is about 6–30 hours, preferably about 16 hours. The alkylation product can be isolated by extractive workup and purified by flash chromatography or high pressure liquid chromatography (HPLC).

Phosphonate ester derivatives of primary or secondary amines but preferably primary amines may also be prepared by standard reductive amination methods as shown in Step A2. In general, the hydroxyalkylphosphonate or bisphosphonate can be oxidized to the aldehyde by treating a solution of oxalyl choride in a typical anhydrous polar solvent such as methylene chloride with excess dimethyl sulfoxide (DMSO), preferably two fold excess, at about −78° C. to about −70° C. under argon. When the bubbling ceases, about 0.8 to 1.0 equivalent of hydroxyalkylphosphonate or bisphosphonate may be added dropwise at about −100° C. to about −70° C., preferably at about −78° C. After stirring for about 5 to 40 minutes, but preferably 15 minutes, about 2.0 to 2.5 equivalents of a base such as triethylamine is added. The resultant reaction mixture is then warmed to about −30° C. after about 5 to 20 minutes. The solution of aldehyde so obtained can be used directly or preferably the aldehyde product can be isolated by standard methods. One skilled in the art will recognize that other methods of oxidation may also be used to obtain said aldehyde. A solution of about 1.0 to 1.6 equivalents, but preferably about 1.2 equivalents, of the primary amine in a polar solvent, preferably methanol is added dropwise to the reaction flask. The mixture can be suitably stirred for 10 to 50 minutes, preferably 20 minutes, then sodium cyanoborohydride is added. The mixture can be stirred 8–30 hours, preferably for 12 to 16 hours. The reaction is quenched with methanolic HCl (pH=3) and then evaporated to near dryness. The product can be isolated by diluting with a polar solvent such as methylene chloride and extractive work up. Purification is typically achieved by flash chromatography or HPLC.

The phosphonosulfonic acids are generally obtained from the phosphonate esters (Step B) by treating a solution of the ester in an aprotic solvent such as THF, DME or ether with about one equivalent of a base such as LDA, butyl lithium, sodium hydride or potassium hexamethyl disilazide at about −100° C. to about −40° C. but preferably at about −78° C. and then treating the resultant solution or suspension with a stream of sulfur trioxide vapour in an anhydrous, inert gas such as nitrogen or argon. The phosphate ester is then hydrolyzed as described for steps C1 and C2 to give the phosphonosulfonic acids.

The phosphonic acids (Step C1) are typically obtained from the phosphonate esters (alkyl or arylalkyl) by treating a solution of the ester in an aprotic solvent such as acetonitrile with excess halotrimethyl silane (about 6–15 equivalents), preferably about 10 equivalents of bromotrimethyl silane at about −10° C. to room temperature from one to six days under an inert atmosphere. The reaction is usually complete after about 2 days at room temperature. The reaction is quenched with methanol and the solution evaporated to give the crude phosphonic acid.

In an alternate method (preferred for aryl esters, Step C2) a strong inorganic base such as sodium hydroxide, lithium hydroxide or potassium hydroxide in a polar solvent such as dioxane, methanol or ethanol may be used to hydrolyze one ester per phosphonate selectively. Suitable temperature ranges are room temperature to 70° C., but preferably 50° C.

Certain compounds of this invention may have at least one asymmetric carbon atom. Further, certain compounds of this invention may exist in their cis or trans configuration. As a result, those compounds of this invention may be obtained either as racemic mixtures, diastereoisomer mixtures or as individual enantiomers. When two or three asymmetric centers are present the product may exist as mixtures of two or four diastereomers. Of course it is understood that certain other compounds within the scope of this invention could have a number of stereocenters. In general, a compound with x stereocenters can have a maximum of $2^x$ stereoisomers. Therefore, a compound having three such centers gives rise to a maximum of eight stereoisomers, while one having four produces sixteen, etc. The product may be synthesized as a mixture of the isomers and then the desired isomer separated by conventional techniques such as chromatography or fractional crystallization from which each diastereomer may be resolved. On the other hand, synthesis may be carried out by known stereospecific processes using the desired form of the intermediate which would result in obtaining the desired stereospecificity.

Reference to the separation of cis and trans isomers by chromatography may be found in W. K. Chan, et al, *J. Am. Chem. Soc.* 96, 3642, 1974.

It is to be understood that the scope of this invention encompasses not only the various isomers which may exist but also the various mixture of isomers which may be formed.

The resolution of the compounds of this invention and their starting materials may be carried out by known procedures. Incorporation by reference is hereby made to the four volume compendium *Optical Resolution Procedures for Chemical Compounds*: Optical Resolution Information Center, Manhattan College, Riverdale, N.Y. Such procedures are useful in the practice of this invention. A further useful reference is *Enantiomers, Racemates and Resolutions*: Jean Jacques, Andre Collet and Samuel H. Wilen; John Wiley & Sons, Inc., New York, 1981. Basically, the resolution of the compounds is based on the differences in the physical properties of diastereomers. Conversion of the racemates into a mixture of diastereomers by attachment of an enantiomerically pure moiety results in forms that are separable by fractional crystallization, distillation or chromatography.

The present compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, oxalic, sulfuric, nitric, benzenesulfonic, toluenesulfonic, acetic, maleic, tartaric and the like which are pharmaceutically acceptable. Basic salts for pharmaceutical use are the Na, K, Ca and Mg salts.

Various substituents on the present new compounds can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups known in the art, may be employed. Examples of many of these possible groups may be found in *"Protective Groups in Organic Synthesis"* by T. W. Green, John Wiley and Sons, 1981. For example, nitro groups can be added by nitration and the nitro group converted to other groups, such as amino by reduction, and halo by diazotization of the amino group and replacement of the diazo group. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

Since the compounds of this invention have certain substituents which are necessarily present, the introduction of each substituent is, of course, dependent on the specific substituents involved and the chemistry necessary for their formation. Thus, consideration of how one substituent would be affected by a chemical reaction when forming a second substituent would involve techniques familiar to the skilled artisan. This would further be dependent on the ring involved.

The compounds of the present invention may be prepared by the following representative examples.

$^1$H and $^{31}$P NMR spectra are measured on Bruker AC-F and ARX 300 MHz spectrometers. $^1$H Chemical shifts are reported in parts per million ($\delta$) with respect to the Me$_4$Si resonance in the solvent indicated. Mass Spectra are run on a Varian MATT-112. Commercially available starting materials, reagents and anhydrous solvents (Aldrich) are used as obtained.

TLC analyses are conducted with E. Merck silica gel F-254 plates and visualized with UV light, phosphomolybdic acid and/or ninhydrin stain. Flash chromatography is run on Kieselgel 60, 70–230 mesh. Reverse-phase chromatography is carried out on a Rainin HPLC System using a Dynamax-60A C18 column (21.4 mm×25 cm, 8 µM). HPLC grade solvents are filtered and degassed prior to use. The eluent is monitored by a UV detector and the desired fractions are frozen and lyophilized.

Preparation 1

Diethyl 3-p-toluenesulfonyloxypropyl-1-phosphonate

A 60% oil dispersion of sodium hydride (5.0 g, 125 mmol) is washed with dry hexane (2×) under argon, cooled in an ice/acetone bath and treated with dry dimethoxyethane (200 mL) followed by dropwise additon of diethyl phosphite (14.9 mL, 115 mmol). After the addition is completed the reaction flask is warmed to room temperature over 2 hours. A solution of 3-(tetrahydropyran-2'-yloxy)- 1-bromopropane (25.6 g, 115 mmol) in anhydrous DME (300 mL) is added and the resulting suspension heated to reflux for 2.5 hours. The reaction is quenched with saturated ammonium chlodde solution (20 mL) and transferred to a separatory funnel with the aid of ethyl acetate (500 mL). The organic layer is washed with saturated sodium chloride solution (100 mL), dried (Na$_2$SO$_4$) and concentrated. Flash chromatography (5% MeOH/methylene chloride) gives diethyl 3-(tetrahydropyran-2'-yloxy)propyl-1-phosphonate (25.3 g, 79%). [p ]$^1$H NMR (CDCl$_3$, 300 MHz): δ1.33 (t, 6H, J=6.7 Hz), 1.4–1.95 (m, 10H), 3.46 (m, 2H), 3.81 (m, 2H), 4.1 (m, 4H), 4.57 (br s, 1H).

Diethyl 3-(tetrahydropyran-2'-yloxy)propyl-1-phosphonate (7.9 g, 29.5 mmol) is dissolved in MeOH, treated with pyridinium p-toluenesulfonate (0.7 g, 2.8 mM) and heated to ~50° C. for 5 hours. The solvent is removed and the residue is purified by flash chromatography (5% MeOH/methylene chloride) to yield diethyl 3-hydroxypropyl-1-phosphonate (4.6 g, 85%); Rf=0.42 (7% MeOH/methylene chloride). The intermediate alcohol (3.22 g, 16.4 mM) is dissolved in anhydrous methylene chloride and treated with DMAP (3.31 g, 27.1 mM) and tosylchloride (4.4 g, 24.6 mM) at room temperature for 3 hours. Standard workup and purification gives the title compound (2.67 g, 46%); Rf= 0.51 (7% MeOH/methylene chloride). $^1$H NMR (CDCl$_3$, 300 MHz): δ1.26 (m, 2H), 1.30 (t, 6H, J=7.14 Hz), 1.75 (m, 2H), 1.95 (m, 2H), 2.45 (s, 3H), 4.08 (m, 6H), 7.35 (d, 2H, J=8.09 Hz), 7.79 (d, 2H).

Preparation 2

Tetraethyl 3-Hydroxypropyl-1,1-bisphosphonate

Diethyl 3-(tetrahydropyran-2'-yloxy)propyl-1-phosphonate (2.71 g, 9.67 mmol), as in preparation 1, is dissolved in anhydrous tetrahydrofuran under argon and cooled in a dry ice/isopropanol bath. The solution is treated dropwise with 1M lithium diisopropyl amide (LDA, 10.2 mL, 10.2 mmol) then stirred for 40 min. Diethylchlorophosphate (1.4 mL, 9.69 mmol) is added dropwise; thirty minutes later the reaction is quenched with saturated ammonium chloride solution. Standard workup and chromatographic purification (methylene chloride/MeOH, 19:1) gives tetraethyl 3-(tetrahydropyran-2'-yloxy)-propyl-1,1-bisphosphonate (2.49 g, 62%).

A portion (0.5 g, 1.36 mmol) is dissolved in MeOH (200 mL); the solution is treated with PPTS (1.2 g, 4.8 mmol) and refluxed for 6 hours. After cooling to room temperature the reaction mixture is transferred to a separatory funnel, diluted with ethyl acetate and washed with saturated NaCl. The aqueous layer is wahed with methylene chloride (2×). The organic layers are combined, dried (Na$_2$SO$_4$), concentrated and the residue chromatographed (5–10% MeOH/methylene chloride) to give the title compound (0.30 g, 77%); Rf=0.36 (10% MeOH/methylene chloride). $^1$H NMR (CDCl$_3$, 300 MHz): δ1.35 (t, 12H, J=6.7 Hz), 2.16 (m, 2H,), 2.64 (tt, 1H, J=6.3, 22.1 Hz), 3.77 (t, 2H, J=5 Hz), 4.0 (br s, 1H), 4.21 (m, 8H).

Preparation 3

Tetramethyl 3-hydroxypropyl-1,1-bisphosphonate

Dimethyl 3-(tetrahydropyran-2'-yloxy)propyl-1-phosphonate (3.7 g, 65%) is prepared from 3-(tetrahydropyran-2'-yloxy)-1-bromopropane (5.14 g, 23 mmol) and dimethyl phosphite (2.22 mL, 24 mmol) as described in preparation 1. $^1$H NMR (CDCl$_3$, 300 MHz): δ1.58–1.64 (m, 4H), 1.67–1.88 (m, 6H), 3.46 (m, 2H), 3.72 (s, 3H), 3.75 (s, 3H), 3.75–3.80 (m, 2H), 4.6 (m, 1H).

Dimethyl 3-(tetrahydropyran-2'-yloxy)propyl-1-phosphonate (3.7 g, 14.7 mmol) is treated with 1M LDA (29.4 ml, 29.4 mmol) and dimethylchlorophosphate* (2.56 g, 17.6 mmol) in the manner described in preparation 2 to give the crude bisphosphonate. Chromatographic purification gives tetramethyl 3-(tetrahydro-pyran-2'-yloxy)propyl-1,1-bisphosphonate (2.9 g, 58%). This material is hydrolyzed with PPTS (0.58 g) as described in preparation 2, then concentrated and chromatographed without aqueous workup to yield the title compound (1.38 g, 63%). $^1$H NMR (CDCl$_3$, 300 MHz): δ2.2 (m, 2H), 2.65 (tt, 1 H, J=6.3, 23 Hz), 3.03 (br s, 1H), 3.85 (m, 14H).

* Dimethyl chlorophosphate is prepared from dimethyl phosphite (8.25 mL, 90 mmol) in carbon tetrachloride (150 mL) by the slow addition of a chlorine gas saturated solution of carbon tetrachloride (160 mL). The resulting yellow solution is stirred at room temperature (30 min.), purged with nitrogen and concentrated under reduced pressure. The resulting oil (12 g, 92%) is neutralized by brief storage over potassium carbonate just prior to use.

Preparation 4

Tetraethyl 3-p-toluenesulfonyloxypropyl-1,1-bisphosphonate

Tetraethyl 3-hydroxypropyl-1,1-bisphosphonate (2.0 g, 6.02 mmol) is dissolved in anhydrous methylene chloride (20 mL) and treated with 4-(N,N-dimethylamino)pyridine (DMAP) (0.47 g, 7.5 mmol), tosylchloride (4.4 g, 12.8 mmol) and pyridine (4 ml) at room temperature for 16 hours. The reaction mixture is diluted with ethyl acetate (400 mL) and washed with dil. HCl (2×50 mL) and saturated bicarbonate solution (50 mL). The organic phase is dried (Na$_2$SO$_4$) and concentrated and the resulting residue is chromatographed (2.5 to 5% MeOH/methylene chloride) to give the title compound (2.0 g, 68%); R$_f$=0.33 (5% MeOH/methylene chloride). $^1$H NMR (CDCl$_3$, 300 MHz): δ1.33 (t, 12H, J=5.9 Hz), 2.26 (m, 2H), 2.46 (tt, 1H, J=6.3, 20.5 Hz), 4.16 (m, 8H), 4.26 (t, 2H, 6 Hz), 7.34 (d, 2H, J=7.8 Hz), 7.79 (d, 2H).

EXAMPLE 1

Diethyl 3-[3'-(4"-Benzoxazol-2'"-ylphenyl)-1',2',5',6'-tetrahydropyridyl]-propylphosphonate To a suspension of sodium hydride (0.019 g, 0.63 mmol) in 0.2 mL of anhydrous THF, under argon, is added a solution of 3-(4'-benzoxazol-2"ylphenyl)-1,2,5,6-tetrahydropyridine (0.10 g, 0.36 mmol) in 5 mL of anhydrous THF via cannula. The slurry is stirred for ten minutes before adding DMPU (44 μLs, 0.36 mmol) then stirred for one hour at room temperature. A solution of diethyl 3-p-toluenesulfonyloxypropyl-1-phosphonate (0.17 g, 0.47 mmol) in 0.3 mL of anhydrous THF is added. The mixture is heated to 50° C. and stirred for 6 hours. At this point tetrabutylammonium iodide (0.029 g, 0.072 mmol) is added and the mixture is stirred an additional 15 hours. The reaction is cooled to room temperature, quenched with water (~10 mL) and diluted with methylene chloride (~20 mL). The organic layer is washed with water (2×10 mL), saturated NaCl solution (1×10 mL), dried (MgSO$_4$) and evaporated. Purification by flash chromatography (95:5:1 chloroform/methanol/triethylamine) gives 0.160 g (98%) of the title compound as a pale yellow oil. IR (KBr) 2992, 1617, 1454, 1243, 1059, 1026, 741 cm$^{-1}$. $^1$H NMR (CDCl$_3$, 300 MHz): δ1.29 (t, 6H, J=7.1 Hz), 1.83 (m, 4H), 2.35 (m, 2H), 2.58 (q, 4H), 3.34 (br s, 2H), 4.05 (m, 4H), 6.25 (br t, 1H), 7.29 (m, 2H), 7.45 (d, 2H, J=8.53 Hz) 7.54 (m, 1H), 7.70 (m, 1H), 8.15 (d, 2H). $^{31}$P NMR (CDCl$_3$, 32 MHz): δ32.2 (s). MS (EI, 70EV) m/z 454 (M$^+$). Anal. calc. for C$_{25}$H$_{31}$N$_2$O$_4$P•H$_2$O: C 63.55, H 7.04, N 5.93. Found: C 63.56, H 6.73, N 5.86.

EXAMPLE 2

3-[3'-(4"-(Benzoxazol-2'"-ylphenyl)-1',2',5',6'-tetrahydropyridyl]-propylphosphonic acid To a stirred solution of diethyl 3-[3'-(4"-benzoxazol-2'"-yl-phenyl)-1',2',5',6'-tetrahydropyridyl]-propylphosphonate (45 mg, 0.10 mmol) in 10 mL of anhydrous acetonitrile at 0°

C. is added trimethylsilyl bromide (0.13 mL, 1.0 mmol). After 24 hours at zero degrees, 1.0 mL of methanol is added and the reaction stirred for five minutes. The solution is then concentrated and the methanol addition/evaporation repeated twice more. Final evaporation left 40 mg of a solid/oil mixture. Methanol is added and the solution filtered to afford 37 mg (95%) of the title compound as its hydrobromide salt.

IR (KBr) 2940, 2727, 1615, 1012, 998, 918, 772 cm$^{-1}$.

$^1$H NMR (DMSO-d$_6$, 300 MHz): δ1.66 (dt, 2H, J=7.44, 25.5 Hz), 2.01 (m, 2H), 2.62 (br s, 2H), 3.33 (br t, 4H), 4.23 (br s, 2H), 6.60 (s, 1H), 7.43 (m, 2H), (d, 2H, J=8.30 Hz), 7.80 (m, 2H), 8.21 (d, 2H).

$^{31}$P NMR (DMSO-d$_6$, 32 MHz): δ25.6 (s). MS (FAB+ion) m/z 399 (M+H).

Anal. calc. for C$_{21}$H$_{23}$N$_2$O$_4$P•HBr•⅓ H$_2$O: C 51.97, H 5.12, N 5.77; Found: C 51.97, H 5.11, N 5.63.

EXAMPLE 3

Tetraethyl 3-[3'-(4"-benzoxazol-2'"ylphenyl)-1'2'5'6'tetrahydropyridyl]propyl-1,1-bisphosphonate A dried sample of the 3-(4'-benzoxazol-2"ylphenyl)-1,2,5,6-tetrahydropyridine (0.44 g, 1.58 mmol) is treated with anhydrous dimethoxyethane (10 mL) under argon. A 60% mineral oil dispersion of sodium hydride (0.053 g, 1.7 mM, washed twice with dry hexane) and DMPU (0.192 μL, 1.57 mmol) are added; the resulting suspension is refluxed for 3 hours. The reaction mixture is treated with tetrabutylammonium iodide (0.131 g, 0.35 mmol) and tetraethyl 3-(p-toluenesulfonyloxy)propyl-1,1-bisphosphonate (0.99 g, 2.03 mmol), dissolved in anhydrous dimethoxyethane (10 mL), then refluxed for 16 hours. The flask contents are quenched with methanol (few drops) then water (~30 mL) and transferred to a separatory funnel with the aid of ethyl acetate (150 mL). The organic layer is washed with saturated NaCl solution (2×30 mL), dried (Na$_2$SO$_4$), concentrated and partially purified by flash chromatography (1:19 to 1:9 methanol/methylene chloride) to yield a beige residue (400 mg): TLC Silica Gel (1:9 methanol/methylene chloride) Rf=0.42. A considerable amount of tetraethyl cyclopropyl-1,1-bisphosphonate is also present, Rf=0.5. The residue is further purified on a Dynamax-60A C18 column (21.4 mm×25 cm, 8 μM) ramping from 0.1% TFA/water to 100% MeOH over 45 min. The titled product is isolated as an oil (0.10 g, 11%); Rt=50 minutes.

$^1$H NMR (CDCl$_3$ 300 MHz): δ1.34 (m, 12H), 2.2 (m, 2H), 2.4 (br s, 2H), 2.65 (m, 2H), 2.77 (m, 2H), 3.4 (s, 2H), 4.18 (m, 8H) 6.32 (br s, 1H), 7.35 (m, 2), 7.51 (d, 2H, 8 Hz), 758 (m, 1H), 8.20 (d, 2H). $^{31}$P NMR (CDCl$_3$, 32 MHz): δ24.2 (s). MS (FAB, +ion) m/z 591 (M+H).

EXAMPLE 4

3-[3'-(4"-benzoxazol-2'"ylphenyl)-1'2'5'6'-tetrahydropyridyl]propyl-1,1-bisphosphonate Tetraethyl 3-[3'-(4"-benzoxazol-2'"ylphenyl)-1'2'5'6'-tetrahydropyridyl]propyl-1,1-bisphosphonate (0.09 g, 0.19 mmol) is treated with trimethylsilyl bromide in a manner described above for 48 hours. The reaction is quenched with MeOH at 0° C. and the residue purified by HPLC (0.05% TFA/H$_2$O to MeOH) to yield the title compound (0.035 g, 48%); Rt=36.4 min.

$^1$H NMR (dil ND$_4$OD): d 2.0 (br s, 2H), 2.27 (br s, 2H), 2.7–3.1 (m, 1H), 2.79, (br s, 2H), 2.91 (br s, 2H), 3.42 (br s, 2H), 6.0 (br s, 1H), 7.08 (d, 2H, 7 Hz), 7.15 (m, 2H), 7.26–7.38 (two m, 2H), 7.55 (d, 2H). $^{31}$P NMR (DMSO-d$_6$, 32 MHz): δ20.8 (s). MS (FAB+ion) m/z 479 (M+H).

Anal. calc. for C$_{21}$H$_{24}$N$_2$O$_7$P$_2$•1.9 H$_2$O: C 49.21, H 5.47, N 5.46 Found: C 48.81, H 4.94, N 5.29.

In a like manner, by the methods described in Examples 3 and 4 are prepared:
(a) 4-[3'-(4"-benzoxazol- 2'"ylphenyl)-1'2'5'6'-tetrahydropyridyl]butyl-1,1-bisphosphonate from tetraethyl 4-(p-toluenesulfonyoxy)butyl-1,1-bisphosphonate and 3 -(4'-benzoxazol-2"ylphenyl)-1,2,5,6-tetrahydropyridine.
(b) 5-[3'-(4"-benzoxazol-2 '"ylphenyl)-1'2'5'6'-tetrahydropyridyl]pentyl-1,1-bisphos-phonate from tetraethyl 5-(p-toluenesulfonyloxy)pentyl-1,1-bisphosphonate and 3-(4'-benzoxazol-2"ylphenyl)-1,2,5,6-tetrahydropyridine.
(c) 3-[3'-(4"-benzoxazol-2'"ylphenyl)-3'-hydroxypiperidin-1'-yl]propyl-1,1-bisphosphonate from tetraethyl 3-(p-toluenesulfonyloxy)propyl-1,1-bisphosphonate and 3-(4'-benzoxazol-2"ylphenyl)-3-hydroxypiperidine.
(d) 3-[3'-(4"-benzoxazol-2'"ylphenyl)piperidin-1'-yl]propyl-1,1-bisphosphonate from tetraethyl 3-(p-toluenesulfonyloxy)propyl-1,1-bisphosphonate and 3-(4'-benzoxazol-2"ylphenyl)piperidine.
(e) 3-[3'-(4"-Napth-2 '"-ylphenyl)-1'2'5'6'-tetrahydropyridyl]propyl-1,1 -bisphosphonate from tetraethyl 3-(p-toluenesulfonyoxy)propyl-1,1-bisphosphonate and 3-(4'-napth-2"-ylphenyl)-1,2,5,6-tetrahydropyridine.
(f) 3-[3 '-(4"-Styrylphenyl)-1',2',5',6'-tetrahydropyridyl]propyl-1,1-bisphosphonate from tetraethyl 3-(p-toluenesulfonyloxy)propyl-1,1-bisphosphonate and 3-(4'-styrylphenyl)- 1,2,5,6-tetrahydropyridine.
(g) 3-{3'-[4"-(2'"-Methoxyquinolin-6'"-yl)phenyl]-1',2',5',6'-tetrahydropyridyl}propyl-1,1-bisphosphonate from 3-(p-toluenesulfonyloxy)propyl- 1,1-bisphosphonate and 3-[4'-(2"-Methoxyquinolin-6"-yl)phenyl]-1,2,5,6-tetrahydropyridine
(h) 3-[3'-(Biphen-4"-yl)-1'2'5'6'-tetrahydropyridyl]propyl-1,1-bisphosphonate from tetraethyl 3-(p-toluenesulfonyloxy)propyl-1,1-bisphosphonate and 3-(biphen-4'-yl)-1,2,5,6,-tetrahydropyridine.
(i) 3-[3'-(3'"-Methoxybiphen-4"-yl)-1'2'5'6'-tetrahydropyridyl]propyl-1,1-bisphosphonate from tetraethyl 3-(p-toluenesulfonyloxy)propyl-1,1-bisphosphonate and 3-(3"methoxybiphen-4'-yl)-1,2,5,6-tetrahydropyridine.
(j) 3-[2'-Methyl-2'-(4"-napth-2'"-ylphenyl)propyl-1,1-bisphos-phonate from tetraethyl 3-(p-toluenesulfonyoxy)propyl-1,1-bisphosphonate and 2-methyl-2-(4 '-napth-2"-ylphenyl)morpholine.

EXAMPLE 5

Tetraethyl 3-[trans-2'-(4"-benzoxazol-2'"-ylbenzyloxy)-cyclohexylamino]-propyl-1,1-bisphosphonate To a solution of oxalyl chloride (0.18 mL, 2.1 mmol) in anhydrous methylene chloride (4 mL) at −70° C. under argon, is added DMSO (0.31 mL, 4.0 mmol) dropwise. After bubbling ceased a solution of tetraethyl 3-hydroxypropyl-1,1-bisphosphonate (0.573 g, 1.7 mmol) in 1.8 mL of anhydrous methylene chloride is added dropwise at −78° C. The resulting cloudy solution is stirred for 15 minutes and triethylamine (0.72 mL, 5.1 mmol) is added. After 5 minutes the reaction is warmed to −30° C. and a solution of trans-2-(4'-benzoxazol-2"-ylbenzyloxy)-cyclohexylamine (0.99 g 2.55 mmol) in 10 mL of anhydrous methanol is added dropwise. After 20 minutes sodium cyanoborohydride (0.087 g, 1.36 mmol) is added and the mixture stirred for 16 hours. The reaction is quenched with 4 mL of methanolic HCl (pH=3) and evaporated to near dryness. The residue is diluted with methylene chloride (100 mL), washed with saturated NaHCO$_3$ solution (3×50 mL) and brine (1×50 mL). The organic layer is dried (MgSO$_4$) and evaporated to give 1.6 g of a crude yellow oil. The oil is purified by HPLC (10 mm×25 cm Dynamax-60A 8 μm C18 reverse phase column) ramping from 0–100% methanol in water over 45 mins with a flow rate of 10 mL/min. The product is obtained as a colorless oil (229 mg, 21%); Rt=50 minutes.

$^1$H NMR (CDCl$_3$, 300 MHz): δ1.24 (d, 2H), 1.30 (t, 6H), 1.31 (t, 6H, J=7.14 Hz), 1.73 (br d, 2H), 2.04 (m, 3H), 2.13 (m, 3H), 2.54 (tt, 1H, J=24.1 Hz, J=6.27 Hz), 2.59 (m, 1H), 2.81 (m, 1H), 2.95 (m, 1H), 3.30 (br s, 1H), 4.14 (m, 8H), 4.57 (d, 1H), 4.73 (d, 1H, J=12.2 Hz), 7.35 (m, 2H), 7.51 (d, 2H), 7.57 (m, 1H), 8.23 (d, 2H, J=8.14 Hz).

Anal. calc. for C$_{31}$H$_{46}$O$_8$N$_2$P$_2$·H$_2$O: C 56.87, H 7.39, N 4.28; Found: C 56.95, H 7.20, N 4.39.

EXAMPLE 6

3-[trans-2'-(4"-Benzoxazol-2"'-ylbenzyloxy)-cyclohexylamino]propyl-1,1-bisphosphonic acid A solution of tetraethyl 3-[trans-2'-(4"-benzoxazol-2"'-ylbenzyloxy)cyclohexylamino]-propyl-1,1-bisphosphonate (170 mg, 0.267 mmol) in 3 mL of anhydrous acetonitrile is treated with TMSBr (0.97 mL, 7.35 mmol) at 0° C. and warmed to RT over six days. Standard workup gives an orange oil which is purified by HPLC (10 mm×25 cm Dynamax-60A 8 μm C18 column) ramping from 10–100% methanol in water over 55 mins with a flow rate of 10 mL/min. After lyophilization the title product is obtained as a white solid (55 mg, 39%); Rt=41 min.

$^1$H NMR (ND$_4$OD/D$_2$O, 300 MHz): δ1.10 (br m, 6H), 1.10 (br m, 6H), 1.67 (br m, 2H0, 1.82 (m, 2H), 2.01 (m, 4H), 2.88 (m, 1H), 3.12 (m, 4H), 3.33 (m, 1H, 4.38 (br s, 2H), 7.18 (m, 2H), 7.25 (d, 2H, J=8.13 Hz), 7.35 (m, 1H), 7.44 (m, 1H), 7.77 (d, 2H).

$^{31}$P NMR (ND$_4$OD/D$_2$O, 32 MHz): δ18.67 (s). MS (FAB+ion) m/z 525 (M+H).

Anal. calc. for C$_{23}$H$_{30}$O$_8$N$_2$P$_2$·½ CF$_3$COOH: C 49.58, H 5.29, N 4.82; Found: C 49.60, H 5.64, N 4.76.

EXAMPLE 7

3-[6'-(4"-Styrlphenyl)-cyclohex-3'-enylamino]propyl-1-phosphonic acid

To a stirred solution of 6-(4'-styrylphenyl)cyclohex-3-enylamine (0.44 g, 1.66 mmol) in methylene chloride (21 mL) and pyridine (10 mL) at 0° C. is added phenyl chloroformate (0.25 g, 1.6 mmol). The reaction is warmed to room temperature and partitioned between methylene chloride and water. The organic extracts are washed with brine, dried (MgSO$_4$) and evaporated. The residue is triturated with diethyl ether and purified by flash chromatography (2% diethyl ether/toluene) to give the intermediate phenyl urethane (0.45 g, 70%); Rf=0.26. MS (FAB+ion) m/z 396 (M+H).

To a stirred solution of trimethylsilyl ethanol (1.2 mmol, 0.14 g) in THF (3.8 mL) under argon at room temperature is added 1M solution of potassium tert-butoxide in THF (1.2 mL, 1.19 mmol) The reaction mixture is stirred for 40 minutes and then added dropwise over 5–10 minutes to a stirred solution of the above phenyl urethane (0.45 g, 1.1 mmol) in THF (3.8 ml) at 5° C. The reaction mixture is stirred at this temperature for 20 minutes and then warmed to room temperature for 16 hours. After refluxing for 40 minutes the reaction is cooled to room temperature and partitioned between ethyl acetate and water; the aqueous phase is extracted twice with ethyl acetate. The combined organic phases are washed with brine, dried (Na$_2$SO$_4$) and concentrated. The residue is purified by flash chromatography (10% ethyl acetate/hexane) to give the intermediate silylethoxy urethane (0.22 g, 48%); Rf=0.56 (20% ethyl acetate/hexane). MS (EI) m/z (419 M+).

To a solution of the silylethoxy urethane (73 mg, 0.17 mmol) in THF (1 mL) under argon is added a 0.5M solution of potassium bistrimethylsilyl amide in toluene (0.34 mL, 0.17 mmol). The reaction is stirred at room temperature for 30 minutes and treated with diethyl 3-p-toluenesulfonyloxypropyl-1-phosphonate (119 mg, 0.34 mmol) in THF (0.5 mL) dropwise. The reaction is stirred at room temperature for 16 hours, heated to reflux for 4 hours then cooled to room temperature and partitioned between methylene chloride and water. The aqueous phase is extracted with methylene chloride (3×) and the combined organic extracts are washed with brine, dried (Na$_2$SO$_4$) and concentrated. The residue is purified by flash chromatography, eluted with 25% hexane/ethyl acetate to give diethyl 3-[N-(2'''-trimethylsilylethoxycarbonyl)-6'-(4"-styrylphenyl)cyclohex- 3'-enylamino]propyl-1-phosphonate (19 mg, 19%).

$^1$H NMR (CDCl$_3$, 300 MHz): δ0.12 (br s, 9H), 0.9 (m, 2H), 1.34 (t, 9H), 1.78 (m, 1H), 2 (m, 1H), 2.4 (m, 2H), 2.95 (m, 2H), 3.25 (m, 1H), 4.12 (m, 8H), 4.42 (m, 1H), 5.75 (br s, 2H), 7.11 (br s, 2H), 7.22 (m, 2H), 7.42 (m, 4H), 7.54 (m, 2H), 7.83 (m, 1H). MS (FAB+ion) m/z 598 (M+H).

A solution of diethyl 3-[N-(2'''-trimethylsilylethoxycarbonyl)-6'-(4"-styrylphenyl)cyclohex- 3'-enylamino]propyl-1-phosphonate (18 mg, 0.03 mmol) in acetonitrile (2 mL) is treated with trimethylsilyl bromide (30.2 mg, 0.197 mmol) in the manner described above. Purification by reverse phase HPLC gives the title compound (7 mg, 59%).

$^1$H NMR (CD$_3$OD, 300 MHz): δ1.6 (m, 2H), 1.83 (m, 2H), 2.46 (br m, 4H), 2.92 (m, 1H), 3.06 (m, 1H), 3.18 (m, 1H), 3.64 (m, 1H), 5.8 (complex AB, 2H), 7.19 (br s, 2H), 7.25 (m, 1H), 7.38 (m, 4H), 7.55 (m, 4H). $^{31}$P NMR (CD$_3$OD, 32 MHz): δ28.9(br s). MS (FAB, +ion) Exact Mass Calc. (M+H): 398.1885 Found (M+H): 398.1903

EXAMPLE 8

Tetraethyl 3-[(6'-(4'''-styrylpbenyl)cyclohex-3'-enylamino]propyl-1,1-bisphosphonate From 3-[6'-(4"-styrylphenyl)cyclohex-3'-enylamine and tetraethy 3-hydroxypropyl- 1,1-bisphosphonate in the manner described above is prepared tetraethyl 3-[6'-(4'''-styrylphenyl)-cyclohex-3'-enylamino]-propyl-1,1-bisphosphonate. During the course of the reaction the pH is maintained between 7 and 8 by the addition of dilute HCl in isopropanol. Crude product is purified by flash chromatography using a gradient elution of 40% acetone in toluene to 100% acetone to yield the title compound (0.20 g, 47%), Rf=0.3.

$^1$H NMR (Acetone-d$_6$, 300 MHz): δ1.3 (br t, 13H) 1.6 (m, 1H), 1.92 (m, 4H), 2.4 (m, 4H), 2.76 (m, 3H), 3.2 (m, 1H), 4.12 (m, 8H), 5.84 (m, 2H), 7.08 (s, 2H) 7.22 (m, 3H), 7.38 (m, 2H), 7.5 (m, 4H).

$^{31}$P NMR (Acetone-d$_6$, 32 MHz) δ24.5. MS (EI) m/z 589 (M+H).

EXAMPLE 9

3-[6'-(4"-Styrylphenyl)cyclohex-3'-enylamino]propyl-1,1-bisphosphonic acid

Tetraethyl 3-[6'-(4"-styrylphenyl)cyclohex-3'-enylamino] propyl-1,1-bisphosphonate (0.127 g, 0.21 mmol) is treated with trimethylsilyl bromide in the manner described above and purified by reversed phase HPLC to give the title compound (46.7 mg, 46.6%).

1H NMR (D$_2$O/ND$_4$OD, 300 MHz) δ1.73–2.4 (m, 7H), 2.72 (m, 1H), 2.86 (m, 2H), 3.06 (m, 1H), 3.25 (m, 1H), 5.7 (m, 2H), 7.2 (bs, 2H), 7.35 (m, 5H), 7.52 ), (m, 4H).

$^{31}$PNMR (D$_2$O/ND$_4$OD, 32 MHz) δ19.7 (br s). MS (FAB, +ion) Exact Mass Calc. (M+H): 478.1548 Found (M+H): 478.1521

Anal. calc. for C$_{25}$H$_{29}$O$_6$NP$_2$•½ CF$_3$COOH: C 51.59, H 5.81, N 2.51 Found: C 51.58, H 5.81, N 2.61.

In a like manner, by the methods described in Examples 5&8 and 6&9, the following are prepared:

(aa) 5-[trans-2'-(4"-Benzoxazol-2'"-ylbenzyloxy)cyclohexylamino]pentyl-1,1-bisphosphonic acid from tetraethyl 5-hydroxypentyl-1,1-bisphosphonate and trans-2-(4'-benzoxazol-2"-ylbenzyloxy)cyclohexylamine.

(bb) 4-[trans-2'-(4"-Benzoxazol-2'"-ylbenzyloxy)cyclohexylamino]butyl-1,1-bisphosphonic acid from tetraethyl 4-hydroxybutyl-1,1-bisphosphonate and trans-2-(4'-benzoxazol-2"-ylbenzyloxy)cyclohexylamine.

(cc) 2-[trans-2'-(4"-Benzoxazol-2'"-ylbenzyloxy)cyclohexylamino]ethyl-1,1-bisphosphonic acid from tetraethyl 2-hydroxyethyl-1,1-bisphosphonate and trans-2-(4'-benzoxazol-2"-ylbenzyloxy)cyclohexylamine.

(dd) 3-[3'-a-(4"-Benzoxazol-2'"-ylbenzyloxy)-2'-a-hydroxycyclohexyl-b-amino]propyl-1,1-bisphosphonic acid from tetraethyl 3-hydroxypropyl-1,1-bisphosphonate and 3-a-(4'-Benzoxazol-2"-ylbenzyloxy)-2-a-hydroxycyclohexyl-b-amine.

(ee) 3-[3'-a-(4"-Benzthiazol-2'"-ylbenzyloxy)-2'-a-hydroxycyclohexyl-b-amino]propyl-1,1-bisphosphonic acid from tetraethyl 3-hydroxypropyl-1,1-bisphosphonate and 3-a-(4'-Benzthiazol-2"-ylbenzyloxy)-2-a-hydroxycyclohexyl-b-amine.

(ff) 3-[1'-(4"-Benzoxazol-2'"-ylbenzyloxy)but-2'-ylamino] propyl-1,1-bisphosphonic acid from tetraethyl 3-hydroxypropyl-1,1-bisphosphonate and 1-(4'-Benzoxazol-2"-ylbenzyloxy)but-2-ylamine.

(gg) 3-{[2'-(4"-Benzoxazol-2'"-ylbenzyloxy)ethyl]-[2-(3'-phenylpropoxy)ethyl]amino}propyl-1,1-bisphosphonic acid from tetraethyl 3-hydroxypropyl-1,1-bisphosphonate and [2-(4'-Benzoxazol-2"-ylbenzyloxy)ethyl]-[2-(3'-phenylpropoxy)ethyl]-amine.

(hh) 3-[2'-(4"-Styrylbenzyloxy)cyclohexylamino]propyl-1,1-bisphosphonic acid from 2-(4'-styrylbenzyloxy)cyclohexylamine and tetraethyl 3-hydroxypropyl-1,1-bisphosphonate.

(ii) 3-[6'-(4"-Benzoxazol-2'"-ylphenyl)-cyclohex-3'-enylamino]propyl-1,1 -bisphosphonic acid from 6-(4'-Benzoxazol-2"-ylphenyl)-cyclohex-3-enylamine and tetraethyl 3-hydroxypropyl-1,1-bisphosphonate.

(jj) 3-(4'-Biphenylamino)propyl-1,1-bisphosphonate from tetraethyl 3-hydroxypropyl-1,1-bisphosphonate and 4-biphentlamine.

(kk) 3-[2'-hydroxy-2'-methyl-2'-(4"-napth-2'"-ylphenyl)ethylamino]propyl-1,1-bisphos-phonate from tetraethyl 3-hydroxypropyl-1,1-bisphosphonate and 2-hydroxy-2-methyl-2-(4'-napth-2'-ylphenyl)ethylamine.

(ll) 3-[3'-(4"-Benzoxazol-2'"-ylbenzyloxy)piperidin-1'-yl] propyl-1,1-bisphosphonic acid from tetraethyl 3-hydroxypropyl-1,1-bisphosphonate and 3-(4'-Benzoxazol-2"-ylbenzyloxy)piperidine.

(mm) 3-[6'-(4"-styrylphenyl)cyclohex-3'-enylamino]propyl-1,1-bisphosphonic acid from 3-hydroxypropyl-1,1-bisphosphonate and 6-(4'-styrylphenyl)cyclohex-3-enylamine.

EXAMPLE 10

Tetramethyl 3-[6'-(4"-styrylphenyl)cyclohex-3'-enylamino]propyl-1,1-bisphosphonate From 6-(4'-styrylphenyl)cyclohex-3-enylamine (0.37 g, 1.36 mmol), tetramethyl 3-oxopropyl-1,1-bisphosphonate and sodium cyanoborohydride (84.6 mg, 1.36 mmol), in the manner described above, is prepared tetramethyl 3-[6'-(4"-styrylphenyl)cyclohex-3'-enylamino]propyl-1,1-bisphosphonate. Flash chromatography purification (5% methanol/methylene chloride) gives the title compound (0.52 g, 72%); Rf=0.33 (7% methanol/methylene chloride).

$^1$H NMR (CDCl$_3$, 300 MHz):δ1.55–2.35 (m, 5H), 2.5 (m, 2H), 2.72 (m, 3H), 3.05 (m, 1H), 3.73 (m, 12H), 5.72 (m, 2H), 7.08 (s, 2H), 7.28 (m, 3H), 7.38 (m, 2H), 7.5 (m, 4H).

$^{31}$P NMR (CDCl$_3$, 32 MHz) δ9.6 (m), 9.8(m). MS (FAB+ ion): m/z 534 (M+H).

EXAMPLES 11 AND 12

Trimethyl and Dimethyl 3-[6'-(4"-styrylphenyl)-cyclohex-3'-enylamino]propyl-1,1-bisphosphonate Tetramethyl 3-[6'-(4"-styrylphenyl)cyclohex-3'-enylamino]propyl-1,1-bisphosphonate (0.1 g, 0.19 mmol) in methanol (2 mL) is treated with 1M aqueous sodium hydroxide (0.38 mL, 0.38 mmol) stirred at room temperature for 3.5 hours, then heated to 60° C. for 12 hours. A further quantity of 1M sodium hydroxide solution (0.38 mL, 0.38 mmol) is added, the reaction heated to reflux for 6 h, then stirred at room temperature for 96 hours. The mixture is concentrated and passed through a small silica column (methylene chloride:ammonium hydroxide:methanol 5:1:4). The products are collected, concentrated and purified by reverse phase HPLC (100% water to 50% acetonitrile in water) to yield trimethyl 3-[6'-(4"-styrylphenyl)cyclohex-3'-enylamino]propyl-1,1-bisphosphonate as the ammonium salt (19.5 mg, 19%) and dimethyl 3-[6'-(4"-styrylphenyl)cyclohex-3'-enylamino]propyl-1,1-bisphosphonate as the ammonium salt (19.5 mg, 19%) and dimethyl 3-[6'-(4'"styrylphenyl)cyclohex-3'-enylamino]propyl-1,1-bisphosphonate (10.5 mg, 10%).

EXAMPLE 11

Trimethylester:
$^1$H NMR(CD$_3$OD, 300 MHz): δ2.1 (m, 2H), 2.3 (m, 2H), 2.48 (m, 4H), 3.21 (m, 3H), (2 s, 3H), (4 s, 6H) 5.8 (complex AB, 2H), 7.19 (bs, 2H), 7.26 (m, 1 H), 7.38 (m, 4H), 7.59 (m, 4H).

$^{31}$P NMR (Acetone-d6, 32 MHz): δ17 (br s), 32 (d). MS (FAB+ion) m/z 520 (M+H). Anal. calc. for $C_{26}H_{35}O_6NP_2 \cdot 2 H_2O$: C 56.20, H 7.08, N 2.52 Found: C 56.36, H 6.79, N 2.44.

EXAMPLE 12

Dimethylester:

$^1$H NMR (CD$_3$OD, 300 MHz): δ1.95–2.75 (m, 8H), 3.04 (m, 1H), 3:16 (m, 1H), 3.29 (m, 1H), 4.57 (br s, 3H), 4.61 (br s, 3H), 5.82 (complex AB, 2H), 7.19 (br s, 2H), 7.23 (m, 1H), 7.39 (m, 4H), 7.58 (m, 4H).

$^{31}$P NMR (CD$_3$OD, 32 MHz) δ20.75 (br s). MS (FAB+ion) m/z 506 (M+H). Anal. calc. for $C_{25}H_{33}O_6NP_2 \cdot \frac{1}{2}NH_3 \cdot \frac{1}{2} H_2O$: C 55.50, H 6.99, N 3.88 Found: C 55.15, H 7.06, N 3.94.

Various tests have been carried out to show the ability of the compounds of the present invention to exhibit pharmacological responses that can be correlated with activity in humans. These tests involve such factors as the effect of the compounds of Formula I to inhibit squalene synthesis. It has been found that compounds within the scope of this invention when tested using the following procedures show a marked activity for the inhibition of squalene synthase and hence are believed to be useful in the treatment of cholesterol-related disorders.

Squalene Synthase Inhibition Assay

The squalene synthase assay used is described by Amin et al. in "Bisphosphonates Used for the Treatment of Bone Disorders Inhibit Squalene Synthase and Cholesterol Biosynthesis," *Journal of Lipid Research*, 33:1657–1663 (1992).

I. Preparation of Assay Substances:

A) Test Solutions:

Test solutions are prepared fresh in 100% DMSO or dH$_2$O. Subsequent dilutions are made in the same solvent. Compounds are tested initially at 1 μM (final concentrations).

B) Assay Buffers:

Potassium Phosphate (50 mM,) pH 7.4, and HEPES (4-(2-hydroxyethyl)-1-piperazineethanesulfonic acid, 50 mM) pH 7.4 stock buffers are prepared and stored at 4° C. until use.

C) Microsomal Enzyme Preparation:

Fresh livers from male Sprague-Dawley rats (Taconic Farms, Germantown, N.Y.) weighing 150–200 g are collected after exsanguination. All subsequent procedures are performed at 4° C. The liver is homogenized in the assay buffer (50 mM, pH 7.4). Cellular fractions are separated as described by Popjak, G. in "Enzymes of sterol biosynthesis in liver and intermediates of sterol biosynthesis," *Meth. Enzymol.* 15:393–454 (1969). Microsomes are prepared by centrifugation (100,000 g) and then resuspended in the assay buffer. Microsomes are rehomogenized with a motor-driven Teflon pestle to yield a uniform suspension (~30 mg protein/ ml), aliquoted, and stored at −80° C. until use.

II. Squalene Synthase Assay

The procedure is a modification of those described by Popjack (ibid) and Poulter et al. in "Squalene synthase. Inhibition by ammonium analogues of carbocationic intermediates in the conversion of presqualene diphosphate to squalene" *J. Am. Chem. Soc.* 111: 3734–3739 (1989). The assay is performed in 1 ml of 50 mM assay buffer, pH 7.4, containing 10 mM MgCl$_2$, 0.5 mM NADPH, microsomes (30 μg protein), a bisphosphonate dissolved in distilled water, and substrate [$^3$H]FPP (0.5 μM, 0.27 Ci/mmol) in a 16×125 mm glass screw-cap tube. All components except [$^3$H]FPP are preincubated for 10 min. at 37° C. The reaction is initiated by the addition of [$^3$H]FPP. After 10 min at 37° C., the reaction is terminated by the addition of 1 ml 15% KOH in ethanol. The tubes are incubated at 65° C. for 30 min. to solubilize proteins. The mixture is extracted with 5 ml petroleum ether for 10 min. After freezing the lower aqueous phase, the organic phase is transferred to glass tubes containing 2 ml distilled water. After washing the lower aqueous phase is frozen and the petroleum ether phase is removed and counted with 10 ml Ready Safe liquid scintillation cocktail using a Beckman LS-9000 scintillation counter. DPM values are adjusted against a blank (no enzyme).

The difference in radioactivity in the presence and absence of the test compound is used to determine the level of inhibition. The IC$_{50}$ values are calculated using a linear regression program of Tallarida and Murray (1987). Tallarida, R. J. and Murray, R. B. *Manual of pharmacologic calculations with computer programs.* Springer-Verlag, 1987.

The following table shows examples of representative compounds of this invention and their test results as determined in the squalene synthase inhibition assay.

| Compound | IC$_{50}$ (as % inhibition) | |
|---|---|---|
| | Phosphate buffer | HEPES buffer |
| (structure with PO$_3$H$_2$) | 35% @ 10 μM | 17 μM |
| (structure with two PO$_3$H$_2$) | 0.4 nM | 4.0 nM |

| Structure | IC$_{50}$ (as % inhibition) | |
|---|---|---|
| | Phosphate buffer | HEPES buffer |
| stilbene-cyclohexene-NH-CH₂CH₂CH₂-PO₃H₂ | 61% @ 5 µM | –2% @ 10 µM |
| stilbene-cyclohexene-NH-CH₂CH₂-CH(PO₃H₂)₂ | 0.31 nM | 0.84 nM |
| stilbene-cyclohexene-NH-CH₂CH₂-CH(PO₃HMe)₂ | | 69% @ 10 µM |
| benzoxazole-phenyl-CH₂-O-cyclohexane-NH-CH₂CH₂-CH(PO₃H₂)₂ | | 13 nM |
| benzoxazole-phenyl-CH₂-O-cyclohexane-NH-CH₂CH₂-CH(PO₃Et₂)₂ | | 14% @ 10 µM |

Compounds within the scope of Formula I have been tested by the foregoing assay procedures and exhibit marked squalene synthase inhibition activity and are useful as hypocholesterolemic or hypolipidemic agents by virtue of their ability to inhibit the biosynthesis of cholesterol. Having such ability, the compounds are incorporated into pharmaceutically acceptable carriers and administered to a patient in need of such cholesterol biosynthesis inhibition. These pharmaceutical formulations contain at least one compound according to this invention.

Treatment with a combination of an HMG-CoA reductase inhibitor and a squalene synthase inhibitor would have a synergistic effect on inhibiting cholesterol biosynthesis. Inhibiting the squalene synthase enzyme and the HMG-CoA reductase enzyme at the same time would most closely resemble the physiological conditions of cholesterol homeostasis. A squalene synthase inhibitor could keep cellular concentrations of farnesyl diphosphate high enough for the synthesis of the small amounts of dolichol, ubiquinone, and the farnesylated proteins required by the cell. This would maintain some feedback regulation of the HMG-CoA reductase enzyme and allow smaller amounts of the HMG-CoA reductase inhibitor to be used.

Other combinations with a squalene synthase inhibitor which could have a synergistic effect for controlling undesirable cholesterol levels in the body include niacin, antihyperlipoproteinemic agents such as gemfibrozil, cholesterol absorption inhibitors, bile acid sequestrants, antioxidants and lipoxygenase inhibitors.

Compounds of the present invention which inhibit squalene synthase may also be of use in combating fungal infections in animals and humans. They may be useful in the treatment of variety of systemic infections and treating tropical infections. They may be also useful as prophylactic agents to prevent systemic and tropical fungal infections. Prevention of fungal overgrowth during antibiotic treatment may also be desirable in some disease syndromes.

Compounds may be tested under a spectrum of activity against a panel of representative yeasts, filamentous fungi and bacterial. The ability of compounds of the invention to inhibit the enzyme squalene synthase in fungi and bacteria may be demonstrated in vitro using (14C)FPP as a substrate under assay conditions similar to those described by S. A. Biller et al. in *J. Medicinal Chemistry* 31(10), 1869–1871 (1988), or Amin (ibid).

The in vitro evaluation of the anti-fungal activity of compounds of the invention can be performed by determining the minimum inhibitory concentration (MIC) which is the concentration of the test compound in a suitable medium at which growth of a particular microorganism fails to occur.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepithelially including transdermal, ophthalmic, sublingual and buccal; topically including ophthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a suffactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent of dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimersal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from about 0.1 to about 1000 mg/day, and preferably from about 10 mg to about 100 mg/day, or from about 0.1 mg to about 50 mg/kg of body weight per day and preferably from about 0.1 to about 20 mg/kg of body weight per day and may be administered in several different dosage units. Higher dosages, on the order of about 2 x to about 4x, may be required for oral administration.

We claim:

1. A compound of the formula:

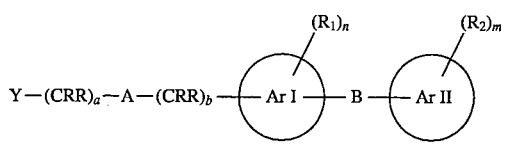

where:

A is O, S, NR, SO, SO₂ or a bond;

B is $(CRR)_{1-2}$, O, S, NR, SO, SO₂, RC=CR, C≡C, O=C or a bond;

Y is

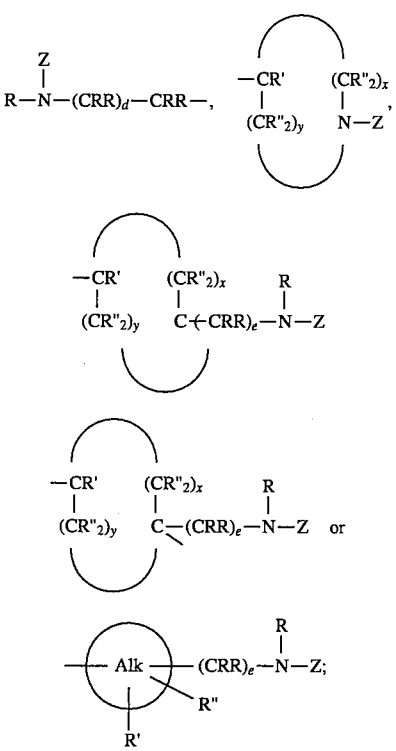

Z is

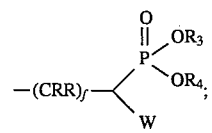

W is H,

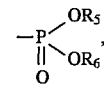

OH, —COOR₇ or SO₃R₈R₉ or;

R is hydrogen or alkyl;

R' and R" are independently hydrogen, alkyl, alkoxy, hydroxy, halo, haloalkyl or phenyl;

R' and R" together may form a double bond;

R₁ and R₂ are independently hydrogen, alkyl, alkoxy, hydroxy, halo, haloalkyl or phenyl;

R₃, R₄, R₅, R₆, R₇, R₈ or R₉ are independently hydrogen, alkyl, aryl, aralkyl or —CH₂OCOR;

Alk is bi- or tri-carbocycloalkane;

Ar I is phenyl;

Ar II is pyridyl, quinolinyl or benzoxazoyl;

a and b are independently 0–3;

a+b is 0–4;

d is 0–3;

a+b+d is 1–3;

e is 0–3;

f is 1–6;

m and n are independently 0–2;

x is 1–6;

y is 0–2;

x+y is 3–6; and its stereoisomers, enantiomers, diastereoisomer and racemic mixtures; or a pharmaceutically acceptable salt thereof.

2. A compound according to claim 1 of the formula:

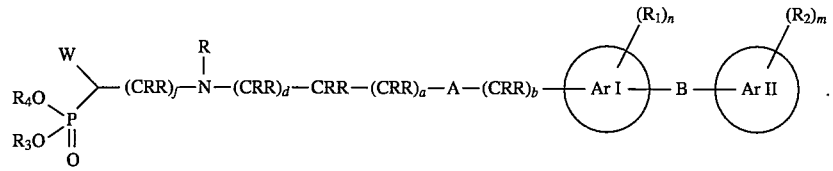

3. A compound according to claim 1 of the formula:

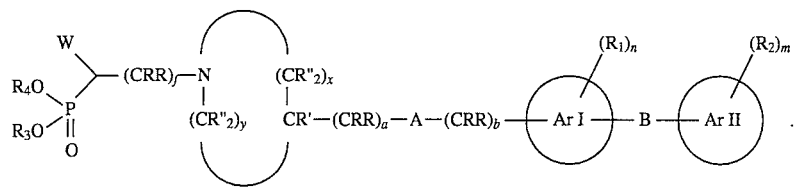
4. A compound according to claim 1 of the formula:
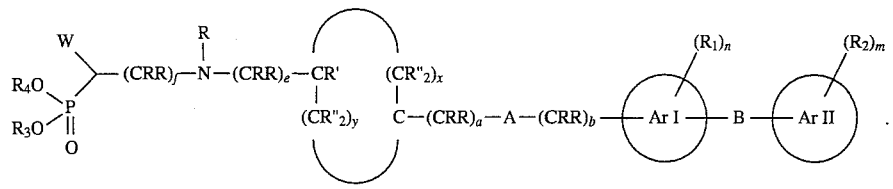
5. A compound according to claim 1 of the formula:
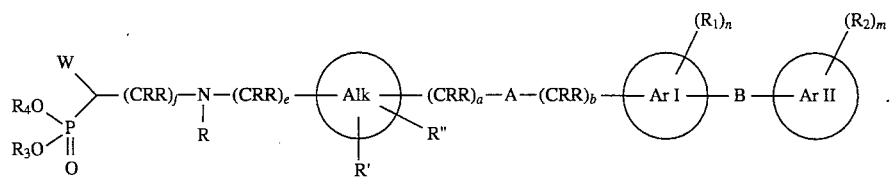
6. A compound according to claim 1 of the formula:
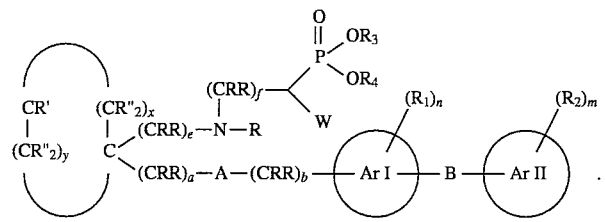
7. A compound according to claim 3 of the formula:
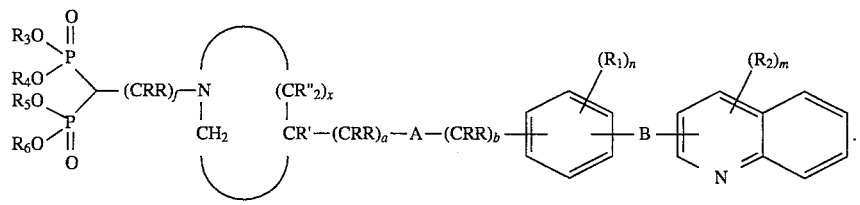
8. A compound according to claim 3 of the formula:
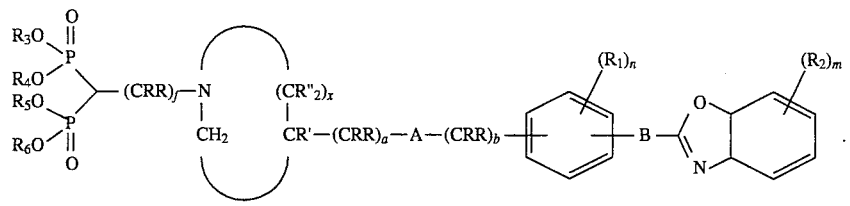
9. A compound according to claim 4 of the formula:

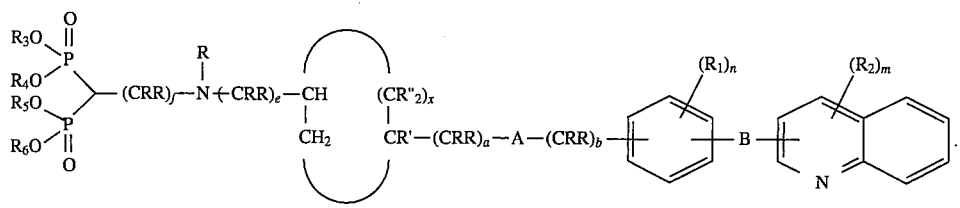

10. A compound according to claim 4 of the formula:

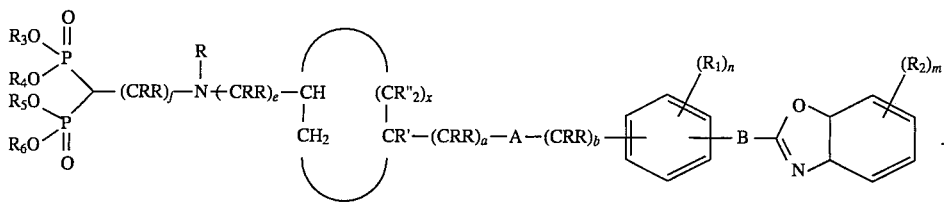

11. A compound according to claim 8 which is diethyl 3-[3'-(4"-benzoxazol-2'"-ylphenyl)-1',2',5',6'-tetrahydropyridyl]propylphosphonate or a pharmaceutically acceptable salt thereof.

12. A compound according to claim 8 which is 3-[3'-(4"-(benzoxazol-2'"-ylphenyl)- 1',2',5',6'-tetrahydropyridyl]propylphosphonic acid or a pharmaceutically acceptable salt thereof.

13. A compound according to claim 8 which is tetraethyl 3-[3'-(4"-benzoxazol-2'"ylphenyl)-1'2'5'6'tetrahydropyridyl]propyl-1,1-bisphosphonate or a pharmaceutically acceptable salt thereof.

14. A compound according to claim 8 which is 3-[3'-(4"-benzoxazol-2'"yiphenyl)-1'2'5'6'-tetrahydropyridyl]propyl-1,1-bisphosphonic acid or a pharmaceutically acceptable salt thereof.

15. A compound according to claim 10 which is tetraethyl 3-[trans-2'-(4"-benzoxazol-2'"-ylbenzyloxy)cyclohexylamino]propyl-1,1-bisphosphonate or a pharmaceutically acceptable salt thereof.

16. A compound according to claim 10 which is 3-[trans-2'-(4"-benzoxazol-2'"-ylbenzyloxy)cyclohexylamino]propyl-1,1-bisphosphonic acid or a pharmaceutically acceptable salt thereof.

17. A method of lowering or maintaining reduced cholesterol levels in a patient requiring such treatment which comprises administering to such patient a squalene synthase inhibitor effective amount of a compound of the formula according to claim 1.

18. A method for inhibiting cholesterol biosynthesis which comprises administering to a patient in need of such inhibition a squalene synthase inhibiting effective amount of a compound according to claim 1.

19. A method according to claim 18 where the patient is in need of a hypocholesterolemic or hypolipidemic agent.

20. A method according to claim 19 for treating atherosclerosis.

21. A pharmaceutical composition comprising a squalene synthase inhibiting effective amount of a compound according to claim 1 in admixture with a pharmaceutical carrier.

22. A pharmaceutical composition according to claim 21 which further includes an HMG CoA reductase inhibitor.

* * * * *